(12) United States Patent
Hawley et al.

(10) Patent No.: US 11,591,315 B2
(45) Date of Patent: Feb. 28, 2023

(54) SUBSTITUTED PYRAZOLE-PYRIMIDINES, VARIANTS THEREOF, AND USES THEREFORE

(71) Applicant: Afferent Pharmaceuticals, Inc., San Mateo, CA (US)

(72) Inventors: Ronald Charles Hawley, San Mateo, CA (US); Prabha Ibrahim, San Mateo, CA (US); Anthony P. Ford, Palto Alto, CA (US); Joel R. Gever, Palo Alto, CA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 13 days.

(21) Appl. No.: 17/179,705

(22) Filed: Feb. 19, 2021

(65) Prior Publication Data

US 2021/0171505 A1 Jun. 10, 2021

Related U.S. Application Data

(63) Continuation of application No. 16/468,446, filed as application No. PCT/US2017/065504 on Dec. 11, 2017, now Pat. No. 10,988,460.

(60) Provisional application No. 62/434,513, filed on Dec. 15, 2016.

(51) Int. Cl.
| | |
|---|---|
| *C07D 403/12* | (2006.01) |
| *C07D 417/12* | (2006.01) |
| *C07D 403/06* | (2006.01) |
| *A61P 11/00* | (2006.01) |
| *A61P 11/06* | (2006.01) |
| *A61P 13/00* | (2006.01) |
| *A61P 29/00* | (2006.01) |

(52) U.S. Cl.
CPC ................. *C07D 403/12* (2013.01)

(58) Field of Classification Search
CPC ................. C07D 403/12; C07D 417/12; C07D 403/06; A61P 11/00; A61P 11/06; A61P 13/00; A61P 29/00
See application file for complete search history.

(56) References Cited

U.S. PATENT DOCUMENTS

| 2007/0049610 A1 | 3/2007 | Dillon et al. |
| 2008/0207619 A1 | 8/2008 | Dillon et al. |
| 2009/0163499 A1 | 6/2009 | Chen et al. |
| 2015/0057299 A1 | 2/2015 | Ford et al. |
| 2016/0185736 A1 | 6/2016 | Kai et al. |
| 2016/0263112 A1 | 9/2016 | Ford et al. |

FOREIGN PATENT DOCUMENTS

WO 2010111059 A1 9/2010

OTHER PUBLICATIONS

Davenport et al., 2011, Scientific Reports, 2021, 13 pages.*
McGarvey et al., 2020, The Lancet, abstract.*
Endometriosis, 2022, https://www.nichd.nih.gov/health/topics/endometri/conditioninfo/treatment.*
EndometriosisPrevention, 2022, https://www.womenshealth.gov/a-z-topics/endometriosis#:~:text=You%20can't%20prevent%20endometriosis,uterus%20during%20your%20menstrual%20cycle.*
RN383149-41-5, registry database compound, 2022.*
RN 1563818-08-5, registry database compound, 2014.*
U.S. Appl. No. 16/468,446, dated Jun. 11, 2019.

* cited by examiner

*Primary Examiner* — Sun Jae Yoo
(74) *Attorney, Agent, or Firm* — Julie M. Lake; Catherine D. Fitch

(57) ABSTRACT

Disclosed herein are substituted pyrazole-pyrimidine compounds of Formula I and variants thereof for the treatment, for example, of diseases associated with P2X purinergic receptors:

In one embodiment, the P2X3 and/or P2X2/3 antagonists disclosed herein are potentially useful, for example, for the treatment of visceral organ, cardiovascular and pain-related diseases, conditions and disorders.

12 Claims, No Drawings

SUBSTITUTED PYRAZOLE-PYRIMIDINES, VARIANTS THEREOF, AND USES THEREFORE

CROSS REFERENCE TO RELATED APPLICATIONS

The present application is a continuation of application No. 16/468,446, filed Jun. 11, 2019, which is the 371 national phase application of International Application No. PCT/US2017/065504, filed Dec. 11, 2017, which claims the benefit of U.S. Provisional Application No. 62/434,513, filed Dec. 15, 2016, hereby incorporated by reference in their entirety.

FIELD OF THE INVENTION

The present disclosure pertains to substituted pyrazole-pyrimidines and variants thereof as defined herein, as well as uses thereof, for example, for the treatment of diseases associated with P2X purinergic receptors, and more particularly to P2X3 and/or P2X2/3 antagonists.

BACKGROUND OF THE INVENTION

The information provided herein and references cited are provided solely to assist the understanding of the reader, and does not constitute an admission that any of the references or information is prior art to the present invention.

Purines, acting via cell surface purinoceptors, have been implicated as having a variety of physiological and pathological roles. ATP, and to a lesser extent, adenosine, can stimulate sensory nerve endings resulting in intense pain and irritation and a pronounced increase in sensory nerve discharge. ATP receptors have been classified into two major families, the P2Y- and P2X-purinoreceptors, on the basis of molecular structure, transduction mechanisms, and pharmacological characterization. The P2Y-purinoceptors are G-protein coupled receptors, while the P2X-purinoceptors are a family of ATP-gated cation channels. Purinergic receptors, in particular, P2X receptors, are known to form homomultimers or heteromultimers. To date, cDNAs for seven P2X subunits have been cloned, (P2X1, P2X2, P2X3, P2X4, P2X5, P2X6 and P2X7), each able to produce homotrimeric channels and some able to form heterotrimeric receptors (e.g. P2X2/3, P2X4/6 and P2X1/5). The structure and chromosomal mapping of mouse and human genomic P2X3 receptor subunits have also been described. In vitro, co-expression of P2X2 and P2X3 receptor subunits is necessary to produce ATP-gated currents with the properties seen in some sensory neurons.

P2X3 receptor subunits are found on primary sensory afferents innervating rodent and human organs and tissues. Data exist suggesting that ATP may be released from epithelial/endothelial cells of the hollow organs or from muscle beds as a result of distention, movement, injury infection and inflammation. ATP released in this manner may serve a role in conveying information to nearby sensory neurons. P2X receptors have been studied in a number of neurons, including sensory, sympathetic, parasympathetic, mesenteric, and central neurons.

Some studies indicate that P2X purinergic receptors play a role in afferent neurotransmission from the many organ systems and tissues, and that modulators of P2X receptors are potentially useful in the treatment of functional organ or tissue disorders and attenuate common chronic symptoms and signs of important diseases or conditions.

Evidence also suggests a role of endogenous ATP and purinergic receptors in nociceptive responses in mice. ATP-induced activation of P2X3 receptors on dorsal root ganglion nerve terminals in the dorsal horn of the spinal cord has been shown to stimulate release of glutamate, a key neurotransmitter involved in nociceptive signalling. P2X3 receptors have been identified on nociceptive neurons in the tooth pulp. ATP released from distressed or damaged cells in many tissue systems may thus lead to pain by activating P2X3 containing receptors on nociceptive sensory nerve endings. This is consistent with observations of the induction of pain and discomfort by intradermally applied ATP in the human blister-base model or following its infusion into a muscle bed. P2X antagonists have been shown to be analgesic in many animal models. This evidence suggests that P2X3 containing channels are involved in the sensitization of nerves that drives and maintains heightened nociception signalling, and that modulators of P2X receptors are potentially useful as inhibitors of sensitization and may have applicability as analgesics, anti-pruritics, antitussives and treatments for autonomic hyperresponsiveness.

The use of antagonists of P2X2 and P2X2/3 for the treatment of pain was discussed by Carter, et al., (*Bioorganic and Medical Chemistry Letters*, 2009, 19(6), 1628-1635; doi:10.1016/j.bmcl.2009.02.003). The structure-activity relationship of a series of diaminopyrimidines was studied. The selectivity of these compounds for P2X3 and P2X2/3 vs. other P2X purinoceptors was also discussed.

Vandenbeuch et al. (*J. Physiol*, 2015, 593(5), 1113-1125; doi: 10/1113/jphysiol.2014.281014) discuss the role of both P2X3 and P2X2/3 channels in taste transduction.

SUMMARY OF THE INVENTION

Disclosed herein are novel compounds of Formula I which are P2X3 and/or P2X2/3 antagonists. Also disclosed herein are uses of these compounds in the potential treatment or prevention of a P2X3 and/or P2X2/3 associated disease or disorder. Also disclosed herein are compositions comprising one or more of the compounds. Further disclosed herein are uses of these compositions in the potential prevention or treatment of a P2X3 and/or P2X2/3 associated disease or disorder.

DETAILED DESCRIPTION OF THE INVENTION

Disclosed herein are compounds of Formula I, or a pharmaceutically acceptable salt thereof:

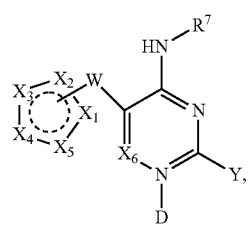

wherein:
ring

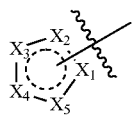

is selected from the group consisting of:

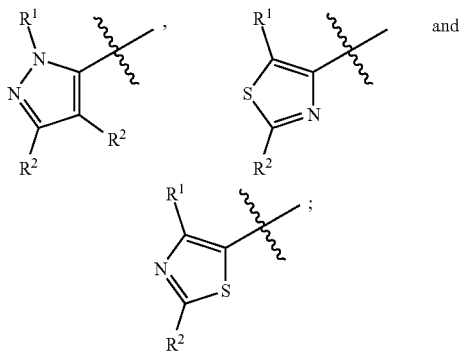

W is CH$_2$, NH, N—C$_{1-6}$alkylene, O or S;
X$_6$ is N or CR$^3$; wherein R$^3$ is hydrogen or C$_{1-12}$alkyl;
Y is hydrogen or —NHR$^d$; wherein R$^d$ is selected from the group consisting of hydrogen, C$_{1-12}$alkyl, C$_{3-12}$cycloalkyl, aryl, and heteroaryl; wherein each of the C$_{1-12}$alkyl, C$_{3-12}$cycloalkyl, aryl, and heteroaryl is optionally substituted with one to three substituents independently selected from halogen, hydroxyl and C$_{1-6}$alkyl;
D is an optional oxygen;
each occurrence of R$^1$ is independently selected from the group consisting of hydrogen, hydroxy, C$_{1-6}$alkyl, C$_{2-6}$alkenyl, and C$_{2-6}$alkynyl; wherein each of the C$_{1-6}$alkyl, C$_{2-6}$alkenyl, and C$_{2-6}$alkynyl is optionally substituted with one to three substituents independently selected from halogen and hydroxyl;
each occurrence of R$^2$ is independently selected from the group consisting of hydrogen, halogen, —NH—R$^f$, —C(O)—NHR$^f$, —C(O)—C$_{1-12}$alkyl, C$_{2-12}$alkenyl, C$_{2-12}$alkynyl, and —O—C$_{1-12}$alkyl;
each occurrence of R$^f$ is independently selected from the group consisting of hydrogen, C$_{1-12}$alkyl, hydroxyl, —SO$_2$—NH$_2$, and —SO$_2$—C$_{1-6}$alkyl; and
R$^7$ is selected from the group consisting of hydrogen, C$_{1-12}$alkyl, and C$_{3-12}$cycloalkyl.
In one embodiment of formula I:
W is CH$_2$ or O;
X$_6$ is N or CH;
Y is hydrogen or —NHR$^d$; wherein R$^d$ is selected from the group consisting of hydrogen or C$_{1-6}$alkyl; wherein the C$_{1-6}$alkyl is optionally substituted with one to three substituents independently selected from halogen and hydroxyl;
D is absent;
each occurrence of R$^1$ is independently selected from the group consisting of hydrogen and C$_{1-6}$alkyl;
each occurrence of R$^2$ is independently selected from the group consisting of hydrogen, halogen, —NH—R$^f$, —C(O)—NHR$^f$, —C(O)—C$_{1-6}$alkyl, C$_{2-6}$alkenyl, and —O—C$_{1-6}$alkyl;

each occurrence of R$^f$ is independently selected from the group consisting of hydrogen, C$_{1-6}$alkyl, hydroxyl, —SO$_2$—NH$_2$, and —SO$_2$—C$_{1-6}$alkyl; and
R$^7$ is selected from the group consisting of hydrogen and C$_{1-6}$alkyl.

In one embodiment, a compound disclosed herein has the following formula Ia:

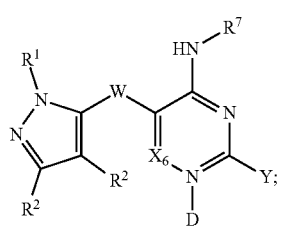

Ia wherein D, W, R$^1$, R$^2$, R$^7$, X$_6$, and Y are as defined above.

In one embodiment, a compound disclosed herein has the following formula Ib:

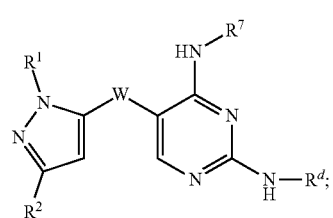

Ib wherein W, R$^1$, R$^2$, R$^7$, and R$^d$ are as defined above.

In one embodiment of a compound having formula I, Ia, or Ib:
W is CH$_2$ or O;
R$^1$ is selected from the group consisting of hydrogen and C$_{1-6}$ alkyl;
R$^2$ is selected from the group consisting of hydrogen, halogen, —NH$_2$, —C(O)—NH$_2$, —C(O)—C$_{1-6}$alkyl, and —O—C$_{1-6}$alkyl; and
R$^d$ is selected from the group consisting of hydrogen and C$_{1-6}$alkyl.

In one embodiment, a compound disclosed herein has one of the following formulae Ic and Id:

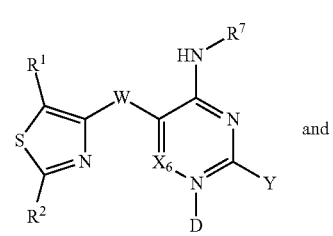

Ic and

-continued

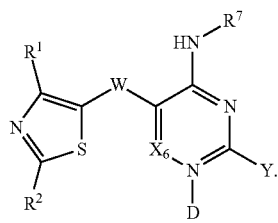

Id

In one embodiment, a compound disclosed herein has formula Ie:

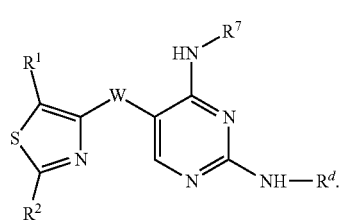

Ie

In one embodiment, a compound disclosed herein has formulae If:

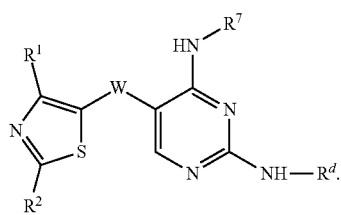

If

In one embodiment of the compound of formula Ie or If:

W is CH$_2$ or O;

R$^1$ is selected from the group consisting of hydrogen and C$_{1-6}$alkyl;

R$^2$ is selected from the group consisting of hydrogen, halogen, —NH$_2$; —C(O)—NH$_2$, —C(O)—C$_{1-6}$alkyl, and —O—C$_{1-6}$alkyl; and R$^d$ is selected from the group consisting of hydrogen and C$_{1-6}$alkyl.

In one embodiment of the compound of formula I, Ia, Ib, Ic, Id, Ie, or If, W is O.

In one embodiment of the compound of formula I, Ia, Ib, Ic, Id, Ie, or If, W is CH$_2$.

In one embodiment, a compound disclosed herein is selected from the group consisting of the compounds exemplified in the Experimental section, or a pharmaceutically acceptable salt thereof.

In one embodiment, disclosed herein are methods for treating a disease mediated by a P2X3 receptor antagonist, a P2X2/3 receptor antagonist, or both, said method comprising administering to a subject in need thereof an effective amount of a compound of Formula I:

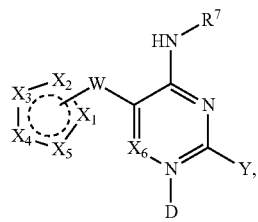

I or a pharmaceutically acceptable salt thereof, wherein:

wherein:

ring

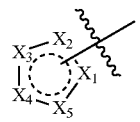

is selected from the group consisting of:

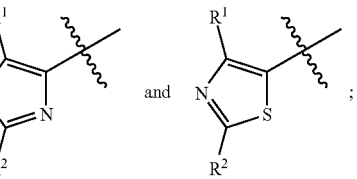

W is CH$_2$, NH, N—C$_{1-6}$alkylene, O or S;

X$_6$ is N or CR$^3$; wherein R$^3$ is hydrogen or C$_{1-12}$alkyl;

Y is hydrogen or —NHR$^d$; wherein R$^d$ is selected from the group consisting of hydrogen, C$_{1-12}$alkyl, C$_{3-12}$cycloalkyl, aryl, and heteroaryl; wherein each of the C$_{1-12}$alkyl, C$_{3-12}$cycloalkyl, aryl, and heteroaryl is optionally substituted with one to three substituents independently selected from halogen, hydroxyl and C$_{1-6}$alkyl;

D is an optional oxygen;

each occurrence of R$^1$ is independently selected from the group consisting of hydrogen, hydroxy, C$_{1-6}$alkyl, C$_{2-6}$alkenyl, and C$_{2-6}$alkynyl; wherein each of the C$_{1-6}$alkyl, C$_{2-6}$alkenyl, and C$_{2-6}$alkynyl is optionally substituted with one to three substituents independently selected from halogen and hydroxyl;

each occurrence of R$^2$ is independently selected from the group consisting of hydrogen, halogen, —NH—R$^f$; —C(O)—NHR$^f$, —C(O)—C$_{1-12}$alkyl, C$_{2-12}$alkenyl, C$_{2-12}$alkynyl, and —O—C$_{1-12}$alkyl;

each occurrence of R$^f$ is independently selected from the group consisting of hydrogen, C$_{1-12}$alkyl, hydroxyl, —SO$_2$—NH$_2$, and —SO$_2$—C$_{1-6}$alkyl; and R$^7$ is selected from the group consisting of hydrogen, C$_{1-12}$alkyl, and C$_{3-12}$cycloalkyl.

Exemplary diseases and conditions that can potentially be treated by a compound disclosed herein include, but are not limited to, disorders of the urinary tract (aka uropathy), disease states associated with the urinary tract (aka urinary tract disease states), overactive bladder (aka detrusor hyperactivity or urge incontinence), outlet obstruction (aka benign prostatic hypertrophy), outlet insufficiency, pelvic hypersensitivity, bladder pain syndrome, endometriosis, respiratory symptoms, cough or urge to cough associated with a respiratory disease, asthma, hypertension, heart failure, dyspnea (aka shortness of breath), sleep apnea, signs and symptoms of carotid body hypertonicity and hyperreflexia (such as breathlessness and fatigue), and sympathetic overactivity in a subject. Additionally, signs and symptoms of upper respiratory tract infection, including the cold and flu symptoms of pharyngitis, rhinitis, nasal congestion, hypertussivity, rhinorrhea and sneezing targeted conditions can potentially be treated by a compound disclosed herein.

In one embodiment, the disease may be a disease associated with pain. The disease associated with pain include, but are not limited to, inflammatory pain, surgical pain, visceral pain, dental pain, premenstrual pain, central pain, pain due to burns, migraine or cluster headaches, nerve injury, neuropathy, neuritis, neuralgias, poisoning, ischemic injury, interstitial cystitis, cancer pain, pain of viral, parasitic or bacterial infection, post-traumatic injury pain, or pain associated with irritable bowel syndrome and inflammatory bowel diseases.

In additional instances the disorders or disease states may include hepatocellular carcinoma, tinnitus, migraine, itch (pruritus), diabetes mellitus, endometriosis and dysmenorrhea, peripheral artery occlusive disease (PAOD), intermittent claudication, acute and chronic heart failure, metabolic syndrome, chronic obstructive pulmonary disease (COPD), atopic dermatitis and other forms of eczema or dermatitis, prurigo nodularis, bursitis, tendonitis, fibromyalgia, gout, joint replacement, lichen sclerosus, psoriasis and psoriatic arthritis, cold sores, kidney stones, gall stones, smell disorders, taste disorders including dysgeusia or burning mouth syndrome, binge eating disorders, hyperphagia, obesity, gastro esophageal reflux disease (GERD), or pain from sickle cell anemia and ischemia.

The present disclosure also provides pharmaceutical compositions comprising the compounds or a pharmaceutically acceptable salt thereof, methods of using the compounds or a pharmaceutically acceptable salt thereof, and methods of preparing the compounds.

Unless otherwise stated, the following terms used in this application, including the specification and claims, have the definitions given herein.

As used in the specification and the appended claims, the singular forms "a", "an" and "the" include plural referents unless the context clearly dictates otherwise.

"Agonist" refers to a compound that enhances the activity of another compound or receptor site.

"Antagonist" refers to a compound that diminishes or prevents the action of another compound or receptor site. Antagonist selectivity for P2X3 subunit containing trimeric channel types, for example, is of increasing interest in the search for therapeutically preferred medicines. This is due to increased understanding, driven by clinical experience with first generation antagonists, of the potential contribution of blockade of distinct trimers with desirable (e.g., efficacy as antitussive, antihypertensive and antihyperalgesic) and less desirable (e.g., tolerability events such as hypogeusia, oropharyngeal dysesthesia) outcomes in treated patients.

As used herein, "alkenyl" refers to both branched- and straight-chain unsaturated aliphatic hydrocarbon groups of 2 to 12 carbon atoms and having at least one carbon-carbon double bond. For example, "$C_{2-6}$alkenyl" refers to an alkenyl group as defined herein having 2 to 6 carbon atoms. Examples of alkenyl groups include, but are not limited to, ethenyl, propenyl, n-butenyl, 3-methylbut-2-enyl, n-pentenyl, octenyl and decenyl. Alkenyl groups may be optionally substituted with one or more substituents as defined herein.

"Alkyl" refers to both branched- and straight-chain saturated aliphatic hydrocarbon groups of 1 to 18 carbon atoms, or more specifically, 1 to 12 carbon atoms. For example, "$C_{1-6}$alkyl" refers to an alkyl group as defined herein having 1 to 6 carbon atoms. Examples of alkyl groups include, but are not limited to, methyl (Me), ethyl (Et), n-propyl (Pr), n-butyl (Bu), n-pentyl, n-hexyl, and the isomers thereof such as isopropyl (i-Pr), isobutyl (i-Bu), sec-butyl (s-Bu), tert-butyl (t-Bu), isopentyl, and isohexyl. Alkyl groups may be optionally substituted with one or more substituents as defined herein.

"Alkylene" means a linear or branched saturated divalent hydrocarbon radical of one to twelve carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkynyl" means a linear monovalent hydrocarbon radical of two to twelve carbon atoms or a branched monovalent hydrocarbon radical of three to twelve carbon atoms, containing at least one triple bond. Examples of alkynyl groups include, but are not limited to, ethynyl (—C≡CH) and 2-propynyl (propargyl, —CH$_2$C≡CH).

"Alkoxy" means a moiety of the formula —OR, wherein R is an alkyl moiety as defined herein. Examples of alkoxy moieties include, but are not limited to, methoxy, ethoxy, iso-propoxy, and the like.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, and ethylenedioxyphenyl, including partially hydrogenated derivatives thereof.

"Cycloalkyl" means a monovalent saturated carbocyclic moiety consisting of mono- or bicyclic rings. Examples of cycloalkyl moieties include, but are not limited to, cyclopropyl, cyclobutyl, cyclopentyl, cyclohexyl, cycloheptyl, and the like, including partially unsaturated derivatives thereof.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

The terms "halo", "halogen" and "halide", which may be used interchangeably, refer to a substituent fluoro, chloro, bromo, or iodo. In some embodiments, halo refers to a fluoro substituent.

"$C_{n-m}$" is used as a prefix before a functional group wherein 'n' and 'm' are recited as integer values (i.e. 0, 1, 2, 12), for example $C_{1-12}$alkyl or $C_{5-12}$heteroaryl. The prefix denotes the number, or range of numbers, of carbons atoms present in the functional group. In the case of ring systems the prefix denotes the number of ring atoms, or range of the number of ring atoms, whether the ring atoms are carbon atoms or heteroatoms. In the case of functional groups made up a ring portion and a non-ring portion (i.e. "arylalkyl" is made up of an aryl portion and an alkyl portion) the prefix is used to denote how many carbon atoms and ring atoms are present in total. For example, with arylalkyl, "$C_7$arylalkyl" may be used to denote "phenyl-$CH_2$—". In the case of some functional groups zero carbon atoms may be present, for example $C_0$aminosulfonyl (i.e. —$SO_2$—$NH_2$, with both potential R groups as hydrogen) the '0' indicates that no carbon atoms are present.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including, e.g., benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present disclosure are inert solvents.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of the present disclosure rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. A person skilled in the art will know how to choose a group for the ease of removal and for the ability to withstand the following reactions.

"Solvates" means solvent additions forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalian class including, but not limited to, humans; non-human primates such as chimpanzees and other apes and monkey species; farm animals such as cows, horses, sheep, goats, and swine; domestic animals such as rabbits, dogs, and cats; laboratory animals in-eluding rodents, such as rats, mice, and guinea pigs; and the like. Examples of non-mammals include, but are not limited to, birds, and the like. The term "subject" does not denote a particular age or sex.

"Disorders of the urinary tract" or "uropathy" used interchangeably with "symptoms of the urinary tract" means the pathologic changes in the urinary tract. Examples of urinary tract disorders include, but are not limited to, incontinence, benign prostatic hypertrophy (BPH), prostatitis, detrusor hyperreflexia, outlet obstruction, urinary frequency, nocturia, urinary urgency, overactive bladder, pelvic hypersensitivity, urge incontinence, urethritis, prostatodynia, cystitis, idiophatic bladder hypersensitivity, and the like.

"Overactive bladder" or "detrusor hyperactivity" includes, but is not limited to, the changes symptomatically manifested as urgency, frequency, altered bladder capacity, incontinence, low micturition threshold, unstable bladder contractions, sphincteric spasticity, detrusor hyperreflexia (neurogenic bladder; dyssynergia), detrusor instability, and the like.

"Outlet obstruction" includes, but is not limited to, benign prostatic hypertrophy (BPH), urethral stricture disease, tumors, low flow rates, difficulty in initiating urination, urgency, suprapubic pain, and the like.

"Outlet insufficiency" includes, but is not limited to, urethral hypermobility, intrinsic sphincteric deficiency, mixed incontinence, stress incontinence, and the like.

"Pelvic Hypersensitivity" includes, but is not limited to, pelvic pain, interstitial (cell) cystitis, prostatodynia, prostatitis, vulvadynia, urethritis, orchidalgia, overactive bladder, and the like.

"Cough" includes acute, sub-acute and chronic cough, treatment-resistant cough, idiopathic chronic cough, post-viral cough, iatrogenic cough, cough associated with post-nasal drip, cough associated with upper respiratory infection, asthma and/or COPD, cough associated with interstitial disease, cough associated with gastroesophageal refjux disease (GERD), cough associated with smoking or a form of bronchitis, neuronal hypeersensitivity underlying acute, sub-acute or chronic cough, and the like.

The term "hypertension" means a condition or disease well known in the art in which the blood pressure in a mammal is chronically elevated. In certain embodiments hypertension may refer to a condition in which a subject's resting systolic blood pressure is above about 120 mmHg and/or diastolic pressure is above about 80 mmHg. In certain embodiments hypertension may refer to a condition in which a subject's resting systolic blood pressure is above about 115 mmHg; or above about 120 mmHg; or above about 125 mmHg; or above about 130 mmHg; or above about 135 mmHg; or above about 140 mmHg; or above about 145 mmHg; or above about 150 mmHg; or above about 155; or above about 160; or above about 165; or above about 170 and/or resting diastolic pressure is above about 75 mmHg; or above about 80 mmHg; or above about 85 mmHg; or above about 90 mmHg; or above about 95 mmHg; or above about 100 mmHg; or above about 105 mmHg; or above about 110 mmHg. In some embodiments hypertension may be primary or secondary hypertension. In some embodiments hypertension may be chronic treatment resistant hypertension, defined as persistent hypertension (resting office blood pressure>140/90 [SBP/DBP]) despite use of 2 or 3 antihypertensive medications including a diuretic, as well as hypertension in patients unable to tolerate currently preferred antihypertensive medications, or in whom approved medications cannot achieve recommended levels of BP control. Diagnosis of hypertension in a subject may in various embodiments be performed by an individual qualified to make such diagnosis in a particular jurisdiction.

The term "heart failure" as used herein refers to a condition or disease well known in the art which is associated with the heart being unable to maintain blood flow sufficient to maintain the needs of the body. Diagnosis of heart failure may in certain embodiments be based on echocardiography results characteristic of heart failure. In some embodiments, heart failure may refer to a condition often referred to as congestive heart failure. In some embodiments, heart failure may refer to systolic heart failure, also called heart failure due to reduced ejection fraction (HFREF) or heart failure due to left ventricular systolic dysfunction. In some embodiments, heart failure may refer to heart failure with preserved ejection fraction (HFPEF) also known as diastolic heart failure or heart failure with normal ejection fraction (HFNEF). In some embodiments, heart failure may be chronic heart failure and in other embodiments the heart failure may be acute heart failure. Diagnosis of heart failure in a subject may in various embodiments be performed by an individual qualified to make such diagnosis in a particular jurisdiction.

The term "dyspnea" as used herein refers to a condition or disease well known in the art in which a subject experiences feelings or sensations associated with impaired breathing. In some embodiments dyspnea may refer to a condition consistent with the America Thoracic Society definition of dyspnea, i.e., "a subjective experience of breathing discomfort that consists of qualitatively distinct sensations that vary in intensity". In some embodiments dyspnea may refer to sensations of inadequate breathing, uncomfortable awareness of breathing and/or breathlessness. Diagnosis of dyspnea in a subject may in various embodiments be performed by an individual qualified to make such diagnosis in a particular jurisdiction.

The term "sleep apnea" as used herein refers to a condition or disease well known in the art characterized by disruptions in breathing (e.g., pauses in breathing or instances of shallow or infrequent breathing, accompanied by ischemia/hypoxemia) during sleep. In some aspects sleep apnea is central sleep apnea, obstructive sleep apnea, or mixed sleep apnea. In some embodiments, sleep apnea may be characterized by more than about 5 apneic events per hour of sleep; or more than about 10 apneic events per hour of sleep; or more than about 15 apneic events per hour sleep; or more than about 20 apneic events per hour of sleep, or more than about 25 apneic events per hour of sleep, or more than about 30 apneic sleep events per hour sleep; or more than about 35 apneic sleep events per hour sleep. Diagnosis of dyspnea in a subject may in various embodiments be performed by an individual qualified to make such diagnosis in a particular jurisdiction.

The term "carotid body" as used herein refers to a small cluster of chemoreceptors and supporting cells located near the fork (bifurcation) of the carotid artery. The carotid body is also referred in the art as carotid glomus or glomus caroticum. The term "altering carotid body tonicity" or activity as used herein means modifying the level of excitation of carotid sinus nerve chemoreceptor afferents that are discharging excessively in response to dysregulated levels of arterial chemicals (hyperreflexia), as well as attenuating the aberrant, spontaneous discharge of such nerve fibers that can occur in the absence of chemical dysregulation (hypertonoicity).

The term "effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as preferred, more preferred and most preferred definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Polymorphism

A compound of Formula I, including a salt or solvate thereof, may exist in crystalline form, non-crystalline form, or a mixture thereof. A compound or a salt or solvate thereof may also exhibit polymorphism, i.e. the capacity of occurring in different crystalline forms. These different crystalline forms are typically known as "polymorphs". Polymorphs have the same chemical composition but differ in packing, geometrical arrangement, and other descriptive properties of crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, all of which may be used for identification. One of ordinary skill in the art will appreciate that different polymorphs may be produced, for example, by changing or adjusting the conditions used in crystallizing/recrystallizing a compound of Formula I.

Optical Isomers-Diastereomers-Geometric Isomers-Tautomers

Included herein are various isomers of the compounds of Formula I. The term "isomers" refers to compounds that have the same composition and molecular weight but differ in physical and/or chemical properties. The structural difference may be in constitution (geometric isomers) or in the ability to rotate the plane of polarized light (stereoisomers).

With regard to stereoisomers, a compound of Formula I may have one or more asymmetric carbon atom and may occur as a racemic mixture or as individual enantiomers or diastereomers. All such isomeric forms are included herein, including mixtures thereof. If a compound of Formula I contains a double bond, the substituent may be in the E or Z configuration. If a compound of Formula I contains a disubstituted cycloalkyl, the cycloalkyl substituent may have a cis- or trans-configuration. All tautomeric forms are also intended to be included.

Any asymmetric atom (e.g., carbon) of a compound of Formula I can be present in racemic mixture or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

A compound of Formula I can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of the final compounds of the examples or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic compounds can also be resolved by chiral chromatography, e.g., high pressure liquid chromatography (HPLC) using a chiral adsorbent.

Some of the compounds described herein may exist with different points of attachment of hydrogen, referred to as tautomers. For example, compounds including carbonyl —$CH_2C(O)$— groups (keto forms) may undergo tautomerism to form hydroxyl —$CH=C(OH)$— groups (enol forms). Both keto and enol forms, individually as well as mixtures thereof, are included within the scope of the present invention.

Isotopic Variations

Compounds of Formula I include unlabeled forms, as well as isotopically labeled forms. Isotopically labeled compounds have structures depicted by the formulae given herein except that one or more atoms are replaced by an atom having a selected atomic mass or mass number. Examples of isotopes that can be incorporated into compounds disclosed herein include isotopes of hydrogen, carbon, nitrogen, oxygen, phosphorous, sulfur, fluorine, iodine and chlorine, such as $^2H$ (i.e., Deuterium or "D"), $^3H$, $^{11}C$, $^{13}C$, $^{14}C$, $^{13}N$, $^{15}N$, $^{15}O$, $^{17}O$, $^{18}O$, $^{32}P$, $^{35}S$, $^{18}F$, $^{123}I$, $^{125}I$ and $^{36}Cl$. The invention includes various isotopically labeled compounds as defined herein, for example those into which radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, substitution with positron emitting isotopes, such as $^{11}C$, $^{18}F$, $^{15}O$ and $^{13}N$, may be particularly desirable for PET or SPECT studies.

Isotopically-labeled compounds of Formula I can generally be prepared by conventional techniques known to those skilled in the art. Furthermore, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index.

Pharmaceutically Acceptable Salts

The term "pharmaceutically acceptable salt" refers to a salt prepared from a pharmaceutically acceptable non-toxic base or acid, including inorganic or organic base and inorganic or organic acid. Salts derived from inorganic bases include aluminum, ammonium, calcium, copper, ferric, ferrous, lithium, magnesium, manganic salts, manganous, potassium, sodium, zinc, and the like. Particular embodiments include ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When a compound of Formula I is basic, a salt may be prepared from a pharmaceutically acceptable non-toxic acid, including an inorganic and organic acid. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, trifluoroacetic acid (TFA) and the like. Particular embodiments include the citric, hydrobromic, hydrochloric, maleic, phosphoric, sulfuric, fumaric, tartaric and trifluoroacetic acids. It will be understood that, as used herein, references to the compounds disclosed herein are meant to also include pharmaceutically acceptable salts thereof.

Methods of Use

Compounds disclosed herein can inhibit activity of the P2X3 and/or P2X2/3 receptors. For example, the compounds disclosed herein can potentially be used to inhibit activity of P2X3 and/or P2X2/3 in cell or in an individual in need of modulation of the enzyme by administering an effective amount of a compound.

A subject administered with a compound disclosed herein, or a pharmaceutically acceptable salt thereof, is generally a mammal, such as a human being, male or female. A subject also refers to cows, sheep, goats, horses, dogs, cats, rabbits, rats, mice, fish, and birds. In one embodiment, the subject is a human.

As used herein, the terms "treatment" and "treating" refer to all processes wherein there may be a slowing, interrupting, arresting, controlling, or stopping of the progression of a disease or disorder that may be associated with P2X3 and/or P2X2/3 enzyme activity. The terms do not necessarily indicate a total elimination of all disease or disorder symptoms. The terms also include the potential prophylactic therapy of the mentioned conditions, particularly in a subject that is predisposed to such disease or disorder.

The terms "administration of" and or "administering a" compound should be understood to include providing a compound described herein, or a pharmaceutically acceptable salt thereof, and compositions of the foregoing to a subject.

The amount of a compound administered to a subject is an amount sufficient to inhibit P2X3 and/or P2X2/3 enzyme activity in the subject. In an embodiment, the amount of a compound can be an "effective amount", wherein the subject compound is administered in an amount that will elicit a biological or medical response of a tissue, system, animal or human that is being sought by a researcher, veterinarian, medical doctor or other clinician. An effective amount does not necessarily include considerations of toxicity and safety related to the administration of a compound. It is recognized that one skilled in the art may affect physiological disorders associated with an P2X3 and/or P2X2/3 enzyme activity by treating a subject presently afflicted with the disorders, or by prophylactically treating a subject likely to be afflicted with the disorders, with an effective amount of a compound disclosed herein, or a pharmaceutically acceptable salt thereof.

An effective amount of a compound will vary with the particular compound chosen (e.g. considering the potency, efficacy, and/or half-life of the compound); the route of administration chosen; the condition being treated; the severity of the condition being treated; the age, size, weight, and physical condition of the subject being treated; the medical history of the subject being treated; the duration of the treatment; the nature of a concurrent therapy; the desired therapeutic effect; and like factors and can be routinely determined by the skilled artisan.

The compounds disclosed herein may be administered by any suitable route including oral and parenteral administration. Parenteral administration is typically by injection or infusion and includes intravenous, intramuscular, and subcutaneous injection or infusion.

The compounds disclosed herein may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound disclosed herein depend on the pharmacokinetic properties of that compound, such as absorption, distribution and half-life which can be determined by a skilled artisan. In addition, suitable dosing regimens, including the duration such regimens are administered, for a compound disclosed herein depend on the disease or condition being treated, the severity of the disease or condition, the age and physical condition of the subject being treated, the medical history of the subject being treated, the nature of concurrent therapy, the desired therapeutic effect, and like factors within the knowledge and expertise of the skilled artisan. It will be further understood by such skilled artisans that suitable dosing regimens may require adjustment given an individual subject's response to the dosing regimen or over time as the individual subject needs change. Typical daily dosages may vary depending upon the particular route of administration chosen. Typical daily dosages for oral administration, to a human weighing approximately 70 kg would range from about 0.1 mg to about 2 grams, or more specifically, 0.1 mg to 500 mg, or even more specifically, 0.2 mg to 100 mg, of a compound of Formula I.

Compositions

The term "composition" as used herein is intended to encompass a dosage form comprising a specified compound in a specified amount, as well as any dosage form which results, directly or indirectly, from combination of a specified compound in a specified amount. Such term is intended to encompass a dosage form comprising a compound of Formula I, or a pharmaceutically acceptable salt thereof, and one or more pharmaceutically acceptable carriers or excipients. Accordingly, the compositions of the present invention encompass any composition made by admixing a compound of the present invention and one or more pharmaceutically acceptable carrier or excipients. By "pharmaceutically acceptable" it is meant the carriers or excipients are compatible with the compound disclosed herein and with other ingredients of the composition.

In one embodiment, disclosed herein is a composition comprising a compound of Formula I, or a pharmaceutically acceptable salt thereof, and one or more pharmaceutically acceptable carriers or excipients. The composition may be prepared and packaged in bulk form wherein an effective amount of a compound of the invention can be extracted and then given to a subject, such as with powders or syrups. Alternatively, the composition may be prepared and packaged in unit dosage form wherein each physically discrete unit contains an effective amount of a compound of Formula I. When prepared in unit dosage form, the composition of the invention typically contains from about 0.1 mg to 2 grams, or more specifically, 0.1 mg to 500 mg, or even more specifically, 0.2 mg to 100 mg, of a compound of Formula I, or a pharmaceutically acceptable salt thereof.

A compound disclosed herein and a pharmaceutically acceptable carrier or excipient(s) will typically be formulated into a dosage form adapted for administration to a subject by a desired route of administration. For example, dosage forms include those adapted for (1) oral administration, such as tablets, capsules, caplets, pills, troches, powders, syrups, elixirs, suspensions, solutions, emulsions, sachets, and cachets; and (2) parenteral administration, such as sterile solutions, suspensions, and powders for reconstitution. Suitable pharmaceutically acceptable carriers or excipients will vary depending upon the particular dosage form chosen. In addition, suitable pharmaceutically acceptable carriers or excipients may be chosen for a particular function that they may serve in the composition. For example, certain pharmaceutically acceptable carriers or excipients may be chosen for their ability to facilitate the production of uniform dosage forms. Certain pharmaceutically acceptable carriers or excipients may be chosen for their ability to facilitate the production of stable dosage forms. Certain pharmaceutically acceptable carriers or excipients may be chosen for their ability to facilitate the carrying or transporting of a compound disclosed herein, once administered to the subject, from one organ or portion of the body to another organ or another portion of the body. Certain pharmaceutically acceptable carriers or excipients may be chosen for their ability to enhance patient compliance.

Suitable pharmaceutically acceptable excipients include the following types of excipients: diluents, lubricants, binders, disintegrants, fillers, glidants, granulating agents, coating agents, wetting agents, solvents, co-solvents, suspending agents, emulsifiers, sweeteners, flavoring agents, flavor masking agents, coloring agents, anti-caking agents, hemectants, chelating agents, plasticizers, viscosity increasing agents, antioxidants, preservatives, stabilizers, surfactants, and buffering agents.

A skilled artisan possesses the knowledge and skill in the art to select suitable pharmaceutically acceptable carriers and excipients in appropriate amounts for the use in the invention. In addition, there are a number of resources available to the skilled artisan, which describe pharmaceutically acceptable carriers and excipients and may be useful in selecting suitable pharmaceutically acceptable carriers and excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The compositions of the invention are prepared using techniques and methods known to those skilled in the art. Some methods commonly used in the art are described in Remington's Pharmaceutical Sciences (Mack Publishing Company).

In one embodiment, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives, (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch) gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as, for example, by coating or embedding particulate material in polymers, wax, or the like.

The compounds disclosed herein may also be coupled with soluble polymers as targetable drug carriers. Such polymers can include polyvinylpyrrolidone, pyrancopolymer, polyhydroxypropylmethacrylamidephenol, polyhydroxyethylaspartamidephenol, or polyethyleneoxidepolylysine substituted with palmitoyl residues. Furthermore, the compounds of the invention may be coupled to a class of biodegradable polymers useful in achieving controlled release of a drug, for example polylactic acid, polepsilon caprolactone, polyhydroxy butyric acid, polyorthoesters, polyacetals, polydihydropyrans, polycyanacrylates and cross-linked or amphipathic block copolymers of hydrogels.

In one embodiment, the invention is directed to a liquid oral dosage form. Oral liquids such as solution, syrups and elixirs can be prepared in dosage unit form so that a given quantity contains a predetermined amount of a compound disclosed herein. Syrups can be prepared by dissolving the compound of the invention in a suitably flavored aqueous solution; while elixirs are prepared through the use of a non-toxic alcoholic vehicle. Suspensions can be formulated by dispersing a compound disclosed herein in a non-toxic vehicle. Solubilizers and emulsifiers such as ethoxylated isostearyl alcohols and polyoxy ethylene sorbitol ethers, preservatives, flavor additives such as peppermint oil or other natural sweeteners or saccharin or other artificial sweeteners and the like can also be added.

In one embodiment, the invention is directed to compositions for parenteral administration. Compositions adapted for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Any open valency appearing on a carbon, oxygen, sulfur or nitrogen atom in the structures herein indicates the presence of a hydrogen atom.

All patents and publications identified herein are incorporated herein by reference in their entirety.

In certain embodiments, $X_1$ is N(iPr), $X_2$ is N; $X_3$ is C—OMe, $X_4$ is CH; $X_5$ is C, and W is $CH_2$, providing compound 100, as follows:

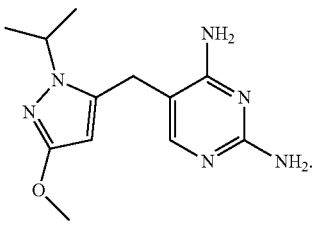

Compound 100

In certain embodiments, $X_1$ is N(Et), $X_2$ is N; $X_3$ is C—OMe, $X_4$ is CH; $X_5$ is C, and W is $CH_2$, providing compound 101, as follows:

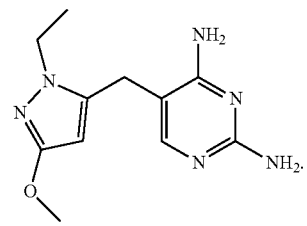

Compound 101

In certain embodiments, $X_1$ is N(Me), $X_2$ is N; $X_3$ is C—OMe, $X_4$ is CH; $X_5$ is C, and W is $CH_2$, providing compound 102, as follows:

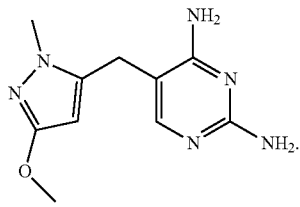

Compound 102

In certain embodiments, $X_1$ is N(iPr), $X_2$ is N; $X_3$ is C—OEt, $X_4$ is CH; $X_5$ is C, and W is $CH_2$, providing compound 103, as follows:

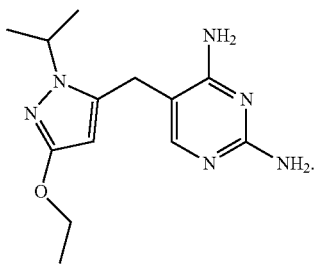

Compound 103

In certain embodiments, $X_1$ is N(Et), $X_2$ is N; $X_3$ is C—OEt, $X_4$ is CH; $X_5$ is C, and W is $CH_2$, providing compound 104, as follows:

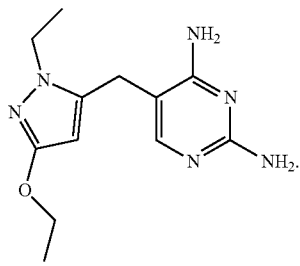

Compound 104

In certain embodiments, $X_1$ is N(Me), $X_2$ is N; $X_3$ is C—OEt, $X_4$ is CH; $X_5$ is C, and W is $CH_2$, providing compound 105, as follows:

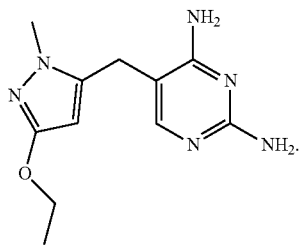

Compound 105

In certain embodiments, $X_1$ is N(iPr), $X_2$ is N; $X_3$ is C—O$^i$Pr, $X_4$ is CH; $X_5$ is C, and W is $CH_2$, providing compound 106, as follows:

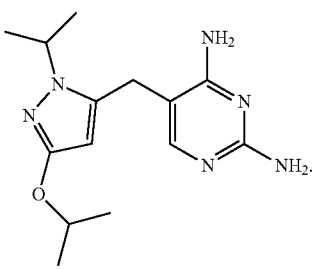

Compound 106

In certain embodiments, $X_1$ is N(Et), $X_2$ is N; $X_3$ is C—O$^i$Pr, $X_4$ is CH; $X_5$ is C, and W is $CH_2$, providing compound 107, as follows:

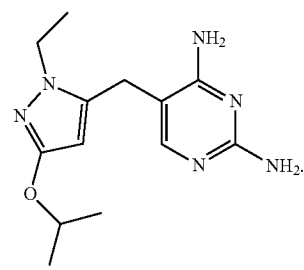

Compound 107

In certain embodiments, $X_1$ is N(Me), $X_2$ is N; $X_3$ is C—O$^i$Pr, $X_4$ is CH; $X_5$ is C, and W is $CH_2$, providing compound 108, as follows:

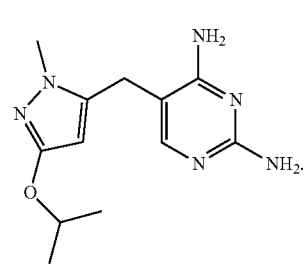

Compound 108

In certain embodiments, $X_1$ is N(iPr), $X_2$ is N; $X_3$ is C(Me), $X_4$ is CH; $X_5$ is C, and W is $CH_2$, providing compound 109, as follows:

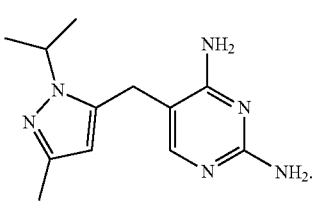

Compound 109

In certain embodiments, $X_1$ is N(Et), $X_2$ is N; $X_3$ is C(Me), $X_4$ is CH; $X_5$ is C, and W is $CH_2$, providing compound 110, as follows:

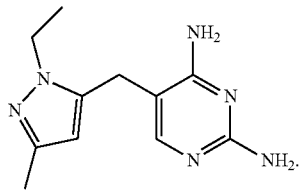

Compound 110

In certain embodiments, $X_1$ is N(Me), $X_2$ is N; $X_3$ is C(Me), $X_4$ is CH; $X_5$ is C, and W is $CH_2$, providing compound 111, as follows:

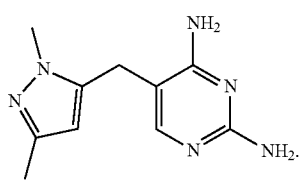

Compound 111

In certain embodiments, $X_1$ is N(Et), $X_2$ is N; $X_3$ is C(Et), $X_4$ is CH; $X_5$ is C, and W is $CH_2$, providing compound 112, as follows:

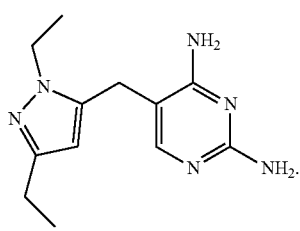

Compound 112

In certain embodiments, $X_1$ is N(iPr), $X_2$ is N; $X_3$ is C(Et), $X_4$ is CH; $X_5$ is C, and W is $CH_2$, providing compound 113, as follows:

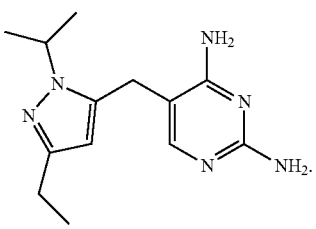

Compound 113

In certain embodiments, $X_1$ is N(Me), $X_2$ is N; $X_3$ is C(Et), $X_4$ is CH; $X_5$ is C, and W is $CH_2$, providing compound 114, as follows:

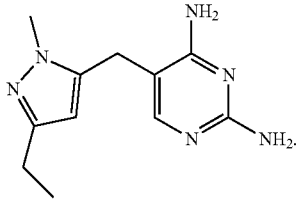

Compound 114

In certain embodiments, $X_1$ is N(iPr), $X_2$ is N; $X_3$ is C(Pr), $X_4$ is CH; $X_5$ is C, and W is $CH_2$, providing compound 115, as follows:

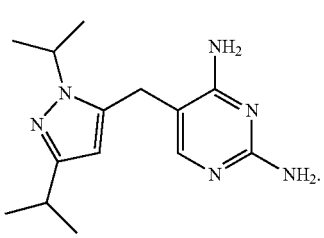

Compound 115

In certain embodiments, $X_1$ is N(Et), $X_2$ is N; $X_3$ is C(Pr), $X_4$ is CH; $X_5$ is C, and W is $CH_2$, providing compound 116, as follows:

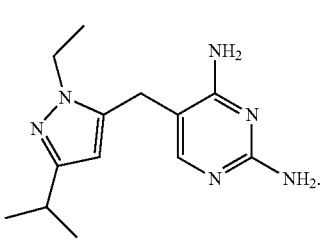

Compound 116

In certain embodiments, $X_1$ is N(Me), $X_2$ is N; $X_3$ is C(Pr), $X_4$ is CH; $X_5$ is C, and W is $CH_2$, providing compound 117, as follows:

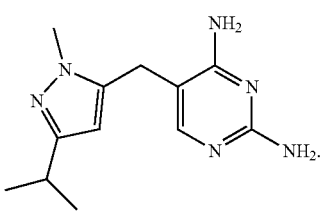

Compound 117

In certain embodiments, $X_1$ is N(R), $X_2$ is N; $X_3$ is C(Me), $X_4$ is CH; $X_5$ is C, and W is O, providing compound 118, as follows:

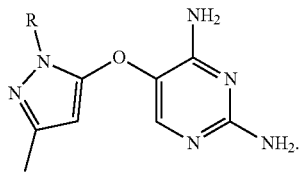

Compound 118

In certain embodiments, $X_1$ is N(R), $X_2$ is N; $X_3$ is C(Et), $X_4$ is CH; $X_5$ is C, and W is O, providing compound 119, as follows:

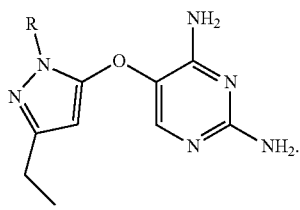

Compound 119

In certain embodiments, $X_1$ is N(R), $X_2$ is N; $X_3$ is C(Pr), $X_4$ is CH; $X_5$ is C, and W is O, providing compound 120, as follows:

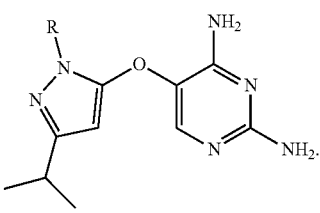

Compound 120

In certain embodiments, $X_1$ is N(R), $X_2$ is N; $X_3$ is C(CO)—$NH_2$, $X_4$ is CH; $X_5$ is C, and W is O, providing compound 121, as follows:

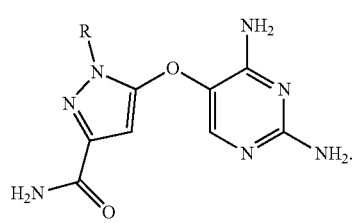

Compound 121

In certain embodiments, $X_1$ is N(R), $X_2$ is N; $X_3$ is C—NH-Me, $X_4$ is CH; $X_5$ is C, and W is $CH_2$, providing compound 122, as follows:

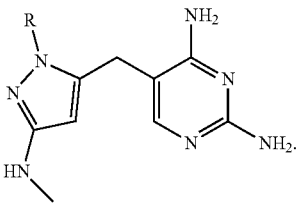

Compound 122

In certain embodiments, $X_1$ is N(R), $X_2$ is N; $X_3$ is C—NH—$SO_2$Me, $X_4$ is CH; $X_5$ is C, and W is $CH_2$, and W is $CH_2$, providing compound 123, as follows:

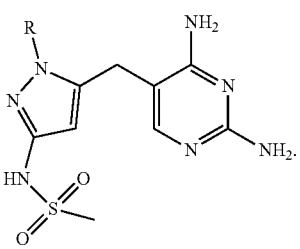

Compound 123

In certain embodiments, $X_1$ is N(R), $X_2$ is N; $X_3$ is C—NH—$SO_2$—$NH_2$, $X_4$ is CH; $X_5$ is C, and W is $CH_2$, providing compound 124, as follows:

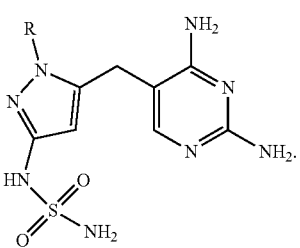

Compound 124

In certain embodiments, $X_1$ is C(iPr), $X_2$ is N; $X_3$ is C(Et), $X_4$ is S; $X_5$ is C; and W is O, providing compound 125, as follows:

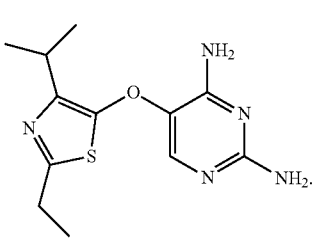

Compound 125

In certain embodiments, $X_1$ is C(iPr), $X_2$ is N; $X_3$ is C(Me), $X_4$ is S; $X_5$ is C, and W is O, providing compound 126, as follows:

Compound 126

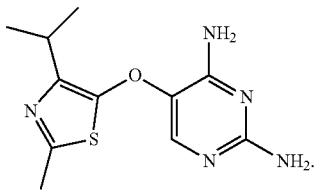

In certain embodiments, $X_1$ is C(Et), $X_2$ is N; $X_3$ is C(Et), $X_4$ is S; $X_5$ is C, and W is O, providing compound 127, as follows:

Compound 127

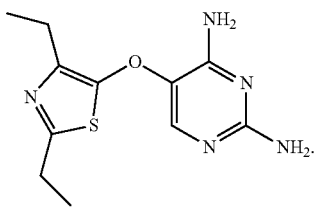

In certain embodiments, $X_1$ is C(Et), $X_2$ is N; $X_3$ is C(Me), $X_4$ is S; $X_5$ is C, and W is O, providing compound 128, as follows:

Compound 128

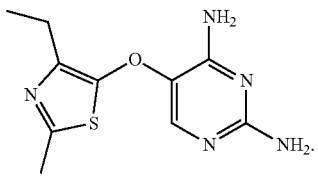

In certain embodiments, $X_1$ is C(iPr), $X_2$ is S; $X_3$ is C(Me), $X_4$ is N; $X_5$ is C, and W is O, providing compound 129, as follows:

Compound 129

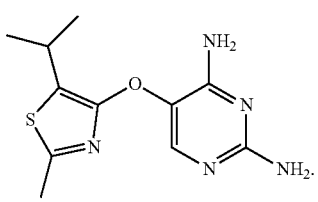

In certain embodiments, $X_1$ is C(iPr), $X_2$ is S; $X_3$ is C(Et), $X_4$ is N; $X_5$ is C, and W is O, providing compound 130, as follows:

Compound 130

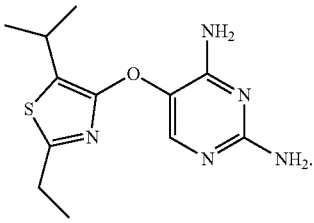

In certain embodiments, $X_1$ is C(Et), $X_2$ is S; $X_3$ is C(Me), $X_4$ is N; $X_5$ is C, and W is O, providing compound 131, as follows:

Compound 131

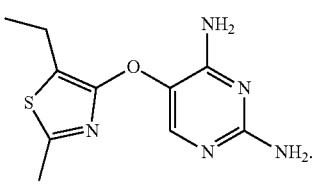

In certain embodiments, $X_1$ is C(Et), $X_2$ is S; $X_3$ is C(Et), $X_4$ is N; $X_5$ is C, and W is O, providing compound 132, as follows:

Compound 132

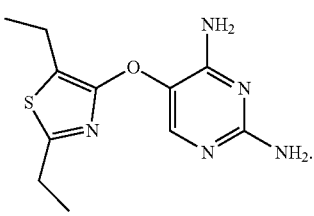

The present disclosure also provides methods for treating a disease or condition by using a P2X3 receptor antagonist, a P2X2/3 receptor antagonist, or both, the method comprising administering to a subject in need thereof an effective amount of a compound of any of Formulae 1 to 5. The disease may be genitourinary disease or urinary tract disease. In other instances the disease may be a disease is associated with pain. The urinary tract disease may be: reduced bladder capacity; frequenct micturition; urge incontinence; stress incontinence; bladder hyperreactivity; benign prostatic hypertrophy; prostatitis; detrusor hyperreflexia; urinary frequency; nocturia; urinary urgency; overactive bladder; pelvic hypersensitivity; urethritis; prostatitits; pelvic pain syndrome; prostatodynia; cystitis; or idiopathic bladder hypersensitivity.

The disease associated with pain may be: inflammatory pain; surgical pain; visceral pain; dental pain; premenstrual pain; central pain; pain due to burns; migraine or cluster headaches; nerve injury; neuritis; neuralgias; neuropathy; poisoning; ischemic injury; interstitial cystitis; cancer pain; viral, parasitic or bacterial infection; post-traumatic injury; pain associated with irritable bowel syndrome, inflammatory bowel disease; or the like.

In certain aspects, the present disclosure also provides methods for treating cough or urge to cough associated with a respiratory disease, hypertension, heart failure, dyspnea, sleep apnea, fatigue, exercise intolerance, by altering carotid body tonicity or activity in a subject, and the like. In additional instances the disorders or disease states may include hepatocellular carcinoma, tinnitus, migraine, itch, diabetes, endometriosis and dysmenorrhea, peripheral artery occlusive disease (PAOD), chronic obstructive pulmonary disease (COPD), atopic dermatitis and other forms of eczema or dermatitis, bursitis, tendonitis, fibromyalgia, gout, joint replacement, lichen sclerosus, psoriasis and psoriatic arthritis, cold sores, kidney stones, gall stones, smell disorders, taste disorders including dysgeusia or burning mouth syndrome, gastro esophageal reflux disease (GERD), binge-eating disorders and obesity, or pain from sickle cell anemia and ischemia.

In some embodiments of the method for treating a disease mediated by a P2X3 receptor antagonist, a P2X2/3 receptor antagonist, or both, comprises administering to a subject in need thereof an effective amount of a compound of any one of Formulae 1 to 5 which shows selectivity for P2X3 vs P2X2/3. For example when the diseases to be treated is medicated by at least the P2X3 receptor, the compound may show greater selectivity for P2X3 than P2X2/3.

In this way the present disclosure may provide a treatment which has reduced side effects, for example reduced taste effects.

Compounds of the present disclosure can be made by a variety of methods. Suitable starting materials and reagents useful in preparing these compounds generally are either available from commercial suppliers, such as Aldrich Chemical Co., or are prepared by methods known to those skilled in the art following procedures set forth in references such as Fieser and Fieser's Reagents for Organic Synthesis; Wiley & Sons: New York, 1991, Volumes 1-15; Rodd's Chemistry of Carbon Compounds, Elsevier Science Publishers, 1989, Volumes 1-5 and Supplementals; and Organic Reactions, Wiley & Sons: New York, 1991, Volumes 1-40.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

The compounds of the present disclosure are usable for the treatment of a wide range of genitourinary diseases, conditions and disorders, including urinary tract disease states associated with bladder outlet obstruction and urinary incontinence conditions such as reduced bladder capacity, frequency of micturition, urge incontinence, stress incontinence, bladder hyperreactivity, benign prostatic hypertrophy (BPH), prostatitis, detrusor hyperreflexia, urinary frequency, nocturia, urinary urgency, overactive bladder, pelvic hypersensitivity, urethritis, prostatitits, pelvic pain syndrome, prostatodynia, cystitis, and idiophatic bladder hypersensitivity, and other symptoms related to overactive bladder.

The compounds of the present disclosure are also useful for the treatment of cough or urge to cough associated with a respiratory disease, hypertension, heart failure, dyspnea, sleep apnea, altering carotid body tonicity or activity in a subject, and the like.

The compounds of the present disclosure are also expected to find utility as analgesics in the treatment of diseases and conditions associated with pain from a wide variety of causes, including, but not limited to, inflammatory pain, surgical pain, visceral pain, dental pain, premenstrual pain, central pain, pain due to burns, migraine or cluster headaches, nerve injury, neuritis, neuralgias, poisoning, ischemic injury, interstitial cystitis, cancer pain, viral, parasitic or bacterial infection, post-traumatic injuries (including fractures and sports injuries), and pain associated with functional bowel disorders such as irritable bowel syndrome.

The present disclosure includes pharmaceutical compositions comprising at least one compound of the present disclosure, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present disclosure will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present disclosure for a given disease.

Compounds of the present disclosure may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by in-halation or insufflation. The preferred manner of administration is generally oral using a convenient daily dosage regimen which can be adjusted according to the degree of affliction.

A compound or compounds of the present disclosure, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

EXPERIMENTAL

The following examples are intended to be illustrative only and not limiting in any way. Abbreviations used are those conventional in the art or the following.

ACN acetonitrile
° C. degree Celsius
DCM dichloromethane
DMA dimethylamine
DMF N,N-dimethylformamide
DMSO dimethylsulfoxide
EtOAc ethyl acetate
EtOH ethanol
g gram(s)
h hour(s)
HPLC high pressure liquid chromatography
kg kilogram(s)
L liter(s)
LC liquid chromatography
LCMS liquid chromatography and mass spectrometry
MeOH methanol
MS mass spectrometry
min minute(s)
mL milliliter(s)
m/z mass to charge ratio
nm nanometer
nM nanomolar
N normal
MR nuclear magnetic resonance
RT room temperature
sat. saturated The following preparations and examples are given to enable those skilled in the art to more clearly understand and to practice the present disclosure. They should not be considered as limiting the scope of the present disclosure, but merely as being illustrative and representative thereof.

Example 1: Synthesis of Compound 1

Compound 1 was made by the synthetic method outlined in Scheme 1:

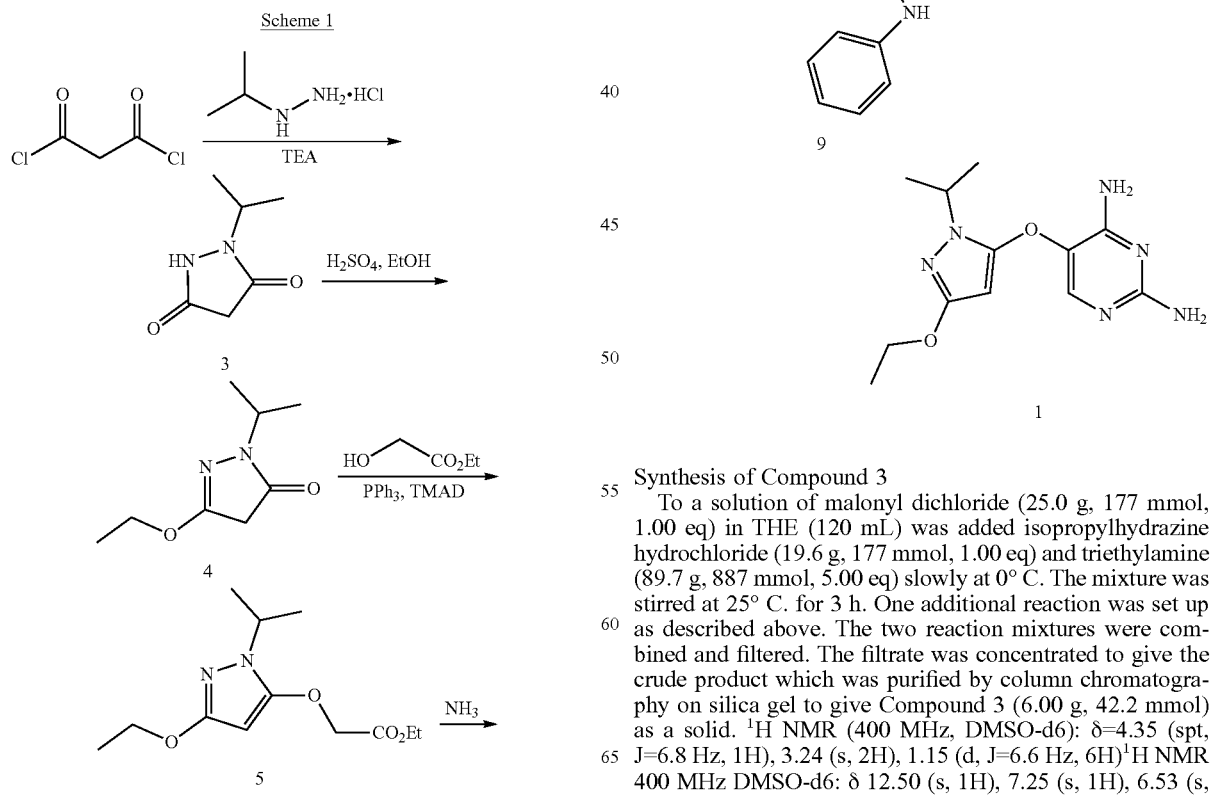

Synthesis of Compound 3

To a solution of malonyl dichloride (25.0 g, 177 mmol, 1.00 eq) in THF (120 mL) was added isopropylhydrazine hydrochloride (19.6 g, 177 mmol, 1.00 eq) and triethylamine (89.7 g, 887 mmol, 5.00 eq) slowly at 0° C. The mixture was stirred at 25° C. for 3 h. One additional reaction was set up as described above. The two reaction mixtures were combined and filtered. The filtrate was concentrated to give the crude product which was purified by column chromatography on silica gel to give Compound 3 (6.00 g, 42.2 mmol) as a solid. $^1$H NMR (400 MHz, DMSO-d6): δ=4.35 (spt, J=6.8 Hz, 1H), 3.24 (s, 2H), 1.15 (d, J=6.6 Hz, 6H)$^1$H NMR 400 MHz DMSO-d6: δ 12.50 (s, 1H), 7.25 (s, 1H), 6.53 (s, 1H), 3.82 (s, 3H), 3.76 (s, 3H), 2.57 (s, 3H).

Synthesis of Compound 4

To a solution of Compound 3 (700 mg, 4.92 mmol) in EtOH (7.00 mL) was added $H_2SO_4$ (145 mg, 1.48 mmol) and the mixture was heated in a microwave reactor at 100° C. for 12 h. One additional reaction was set up as described above. The two reaction mixtures were combined and the pH was adjusted to between 6 and 7 with saturated aqueous $Na_2CO_3$ solution.

The mixtures were concentrated to remove most of EtOH and partitioned between DCM (80 mL) and water (80 mL). The aqueous layer was extracted with DCM (3×50 mL). The combined organic layers were dried over $Na_2SO_4$, filtered and concentrated under reduced pressure. The crude product was purified by column chromatography on silica gel to give Compound 4 (600 mg, 3.53 mmol) as an oil. $^1$H NMR (400 MHz, DMSO-d6): δ=4.35-4.23 (m, 1H), 4.20-4.12 (m, 2H), 3.51-3.46 (m, 2H), 1.29 (t, J=7.1 Hz, 3H), 1.16 (d, J=6.6 Hz, 6H)

Synthesis of Compound 5

To a solution of Compound 4 (1.30 g, 7.64 mmol, 1.00 eq) in THF (12.0 mL) was added ethyl 2-hydroxyacetate (1.19 g, 11.5 mmol, 1.50 eq), $PPh_3$ (2.40 g, 9.17 mmol, 1.20 eq) and TMAD (1.58 g, 9.17 mmol, 1.20 eq). The mixture was stirred at 70° C. for 12 h. The mixture was filtered and the filter cake was washed with petroleum ether (5×3 mL). The filtrates were combined and white suspension appeared. The suspension was filtered off and the filtrate was concentrated to give Compound 5 (1.70 g, crude) as an oil which was used in the next step directly.

Synthesis of Compound 6

Two reactions were carried out in parallel and combined for purification.

Procedure for the first reaction: To a solution of Compound 5 (100 mg, 390 umol, 1.00 eq) in MeOH (0.5 mL) was added $NH_3$/MeOH (2 mL, 20 N) at 0° C. The solution was stirred at 25° C. for 15 h. The reaction mixture was concentrated.

Procedure for the second reaction: To the solution of Compound 5 (1.60 g, 6.24 mmol, 1.00 eq) in MeOH (3.00 mL) was added $NH_3$/MeOH (31 mL, 20 N) at 0° C. The solution was stirred at 25° C. for 15 h. The reaction mixture was concentrated. The residues from the first and second reactions were combined. The residue was purified via prep HPLC to give Compound 6 (550 mg, 2.42 mmol) as a white solid.

Synthesis of Compound 7

Three reactions were carried out in parallel and combined for purification.

Procedure for the first reaction: To a solution of Compound 6 (50.0 mg, 220 umol, 1.00 eq) and TEA (75.7 mg, 748 umol, 3.40 eq) in $CHCl_3$ (1.00 mL) was added TFAA (78.6 mg, 374 umol, 1.70 eq) at 0° C. The mixture was stirred at 25° C. for 1.5 h.

Procedure for the second reaction: To a solution of Compound 6 (50.0 mg, 220 umol, 1.00 eq) and TEA (75.7 mg, 748 umol, 3.40 eq) in $CHCl_3$ (1.00 mL) was added TFAA (78.6 mg, 374 umol, 1.70 eq) at 0° C. The mixture was stirred at 25° C. for 1.5 h.

Procedure for the third reaction: To a solution of Compound 6 (350 mg, 1.54 mmol, 1.00 eq) and TEA (468 mg, 4.62 mmol, 3.00 eq) in $CHCl_3$ (1.40 mL) was added TFAA (485 mg, 2.31 mmol, 1.50 eq) at 0° C. The mixture was stirred at 25° C. for 1 h.

All three reaction mixtures were combined and partitioned between DCM (5 mL) and water (8 mL). The aqueous layer was extracted with DCM (3×5 mL). The combined organic layers were dried over $Na_2SO_4$, filtered and concentrated under reduced pressure. The residue was purified by prep-TLC to give Compound 7 (150 mg, 717 umol) as an oil. $^1$H NMR (400 MHz, CHLOROFORM-d): δ=5.15 (s, 1H), 4.74 (s, 2H), 4.47-4.33 (m, 1H), 4.18-4.09 (m, 2H), 1.39-1.35 (m, 8H).

Synthesis of Compound 8

Compound 7 (100 mg, 478 umol, 1.00 eq) was added to DMF-DMA (3.00 mL). The mixture was stirred at 130° C. for 12 h. The mixture was concentrated under reduced pressure to give Compound 8 (100 mg, crude) as brown oil which was used in the next step directly.

Synthesis of Compound 9

To a solution of Compound 8 (120 mg, 454 umol, 1.00 eq) in DMF (1.00 mL) was added aniline hydrochloride (118 mg, 908 umol, 115 uL). The mixture was stirred at 110° C. for 3 h. The mixture was partitioned between MTBE (5 mL) and water (5 mL). The aqueous layer was extracted with MTBE (3×3 mL). The combined organic layer was dried over $Na_2SO_4$, filtered and concentrated under reduced pressure to give Compound 9 (200 mg, crude) as an oil which was used in the next step directly.

Synthesis of Compound 1

To a solution of Compound 9 (200 mg, 640 umol, 1.00 eq) in n-BuOH (2.00 mL) was added $K_2CO_3$ (177 mg, 1.28 mmol, 2.00 eq) and guanidine hydrochloride (122 mg, 1.28 mmol, 2.00 eq). The mixture was stirred at 110° C. for 12 h and cooled. The mixture was purified by prep-HPLC to give Compound 1 (20.0 mg, 71.9 umol) as a solid. $^1$H NMR (400 MHz, DMSO-d6): δ=7.60 (s, 1H), 6.48 (s, 2H), 5.91 (s, 2H), 4.83 (s, 1H), 4.49 (quin, J=6.6 Hz, 1H), 3.99 (q, J=7.1 Hz, 2H), 1.31 (d, J=6.6 Hz, 6H), 1.22 (t, J=7.1 Hz, 3H) m/z=279.0 $(M+1)^+$ Example 2: Synthesis of Compound 2

Compound 2 was made by the synthetic method outlined in Scheme 2:

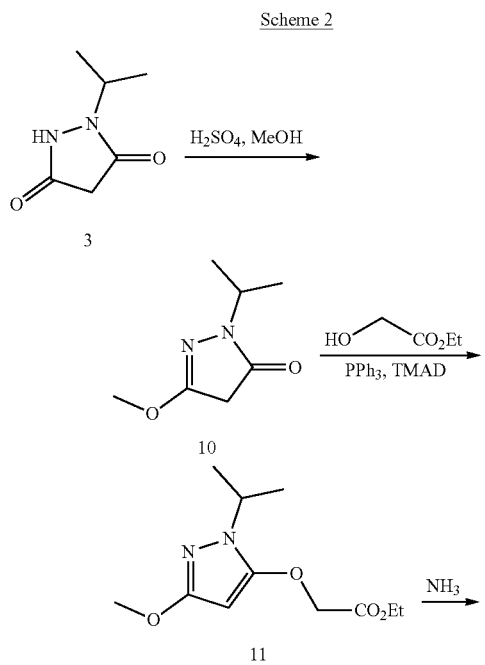

Scheme 2

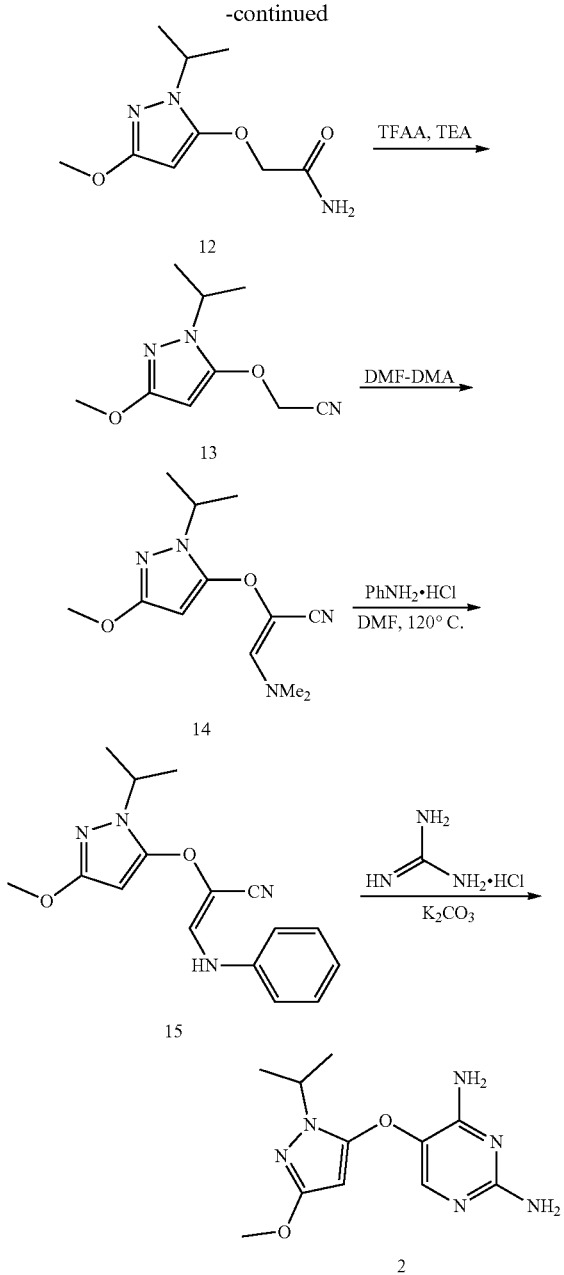

Synthesis of Compound 10

To a solution of Compound 3 (1.00 g, 7.03 mmol, 1.00 eq) in MeOH (10.0 mL) was added $H_2SO_4$ (207 mg, 2.11 mmol, 0.30 eq) at 25° C. The mixture was heated in a microwave reactor at 100° C. for 6 h. One additional reaction was set up as described above. The two reaction mixtures were combined and the pH adjusted to between 6 and 7 with saturated aqueous $Na_2CO_3$. The mixture was concentrated to remove most of the MeOH. Then the residue was partitioned between DCM (50 mL) and water (80 mL) and the aqueous layer was extracted with DCM (3×30 mL). The combined organic layers were dried over $Na_2SO_4$, filtered and concentrated under reduced pressure. The residue was purified by column chromatography on silica gel to give Compound 10 (1.10 g, 7.04 mmol) as an oil. $^1$H NMR (400 MHz, DMSO-d6): δ=4.34-4.24 (m, 1H), 3.79 (s, 3H), 3.67-3.64 (m, 1H), 3.49 (s, 2H), 1.17 (d, J=6.6 Hz, 6H).

Synthesis of Compound 11

To a solution of Compound 10 (1.10 g, 7.04 mmol, 1.00 eq) in THF (15.0 mL) was added ethyl 2-hydroxyacetate (1.10 g, 10.6 mmol, 1.50 eq), TMAD (1.82 g, 10.6 mmol, 1.50 eq) and $PPh_3$ (2.77 g, 10.6 mmol, 1.50 eq). The mixture was stirred at 70° C. for 12 h. The mixture was filtered and the filter cake was washed with petroleum ether (3×10 mL). The filtrates were combined and white precipitate appeared. The precipitate was filtered off and the filtrate was concentrated to give Compound 11 (1.90 g, crude) as an oil which was used in the next step directly. $^1$H NMR (400 MHz, CHLOROFORM-d): δ=4.95 (s, 1H), 4.56 (s, 2H), 4.47 (td, J=6.8, 13.3 Hz, 1H), 4.25 (q, J=7.1 Hz, 2H), 3.83-3.80 (m, 3H), 1.39 (d, J=6.6 Hz, 6H), 1.31-1.27 (m, 3H).

Synthesis of Compound 12

To a solution of $NH_3$ (10 M, 15.7 mL, 20.0 eq) in MeOH (20.0 mL) was added Compound 11 (1.90 g, 7.84 mmol, 1.00 eq) and the mixture was stirred at 25° C. for 12 h. The mixture was concentrated and purified by column chromatography on silica gel. The crude product was purified by prep-HPLC to give Compound 12 (800 mg, 3.75 mmol) as a solid. $^1$H NMR (400 MHz, CHLOROFORM-d): δ=6.28 (brs, 1H), 5.85 (brs, 1H), 5.05 (s, 1H), 4.52 (s, 2H), 4.41 (spt, J=6.7 Hz, 1H), 3.85-3.81 (m, 3H), 1.40 (d, J=6.6 Hz, 6H).

Synthesis of Compound 13

To a solution of Compound 12 (180 mg, 844 umol, 1.00 eq) and TEA (342 mg, 3.38 mmol, 4.00 eq) in $CHCl_3$ (2.00 mL) was added TFAA (355 mg, 1.69 mmol, 2.00 eq) at 0° C. The mixture was stirred at 25° C. for 1.5 h. Two additional reactions were set up as described above. The three mixtures were combined and partitioned between DCM (15 mL) and water (10 mL). The aqueous layer was extracted with DCM (3×10 mL). The combined organic layers were dried over $Na_2SO_4$, filtered and concentrated under reduced pressure. The residue was purified by prep-TLC to give Compound 13 (180 mg, 922 umol) as an oil. $^1$H NMR (400 MHz, CHLOROFORM-d): δ=5.16 (s, 1H), 4.74 (s, 2H), 4.43-4.33 (m, 1H), 3.86-3.83 (m, 3H), 1.38 (d, J=6.6 Hz, 6H).

Synthesis of Compound 14

A mixture of Compound 13 (110 mg, 563 umol, 1.00 eq) in DMF-DMA (2.00 mL) was stirred at 130° C. for 12 h. Two additional reactions were set up as described above. All three mixtures were combined and concentrated under reduced pressure to give Compound 14 (130 mg, crude) as an oil which was used in the next step directly.

Synthesis of Compound 15

To a solution of Compound 14 (130 mg, 519 umol, 1.00 eq) in DMF (1.30 mL) was added aniline hydrochloride (135 mg, 1.04 mmol, 2.00 eq) and the mixture was stirred at 120° C. for 2 h. One additional reaction was set up as described above. The two mixtures were cooled and combined and partitioned between MTBE (3 mL) and water (3 mL). The aqueous layer was extracted with MTBE (3×2 mL). The combined organic layers were dried over $Na_2SO_4$, filtered and concentrated under reduced pressure. The residue was purified by prep-TLC to give Compound 15 (60.0 mg, 201 umol) as an oil.

Synthesis of Compound 2

To a solution of Compound 15 (50.0 mg, 168 umol, 1.00 eq) in n-BuOH (0.5 mL) was added $K_2CO_3$ (46.3 mg, 335 umol, 2.00 eq) and guanidine hydrochloride (32.0 mg, 335 umol, 2.00 eq). The mixture was stirred at 110° C. for 12 h. One additional reaction was set up as described above. The two mixtures were combined and purified by prep-HPLC to give Compound 2 (22.0 mg, 83.3 umol) as a solid. $^1$H NMR (400 MHz, DMSO-d6): δ=7.61 (s, 1H), 6.49 (s, 2H), 5.92 (s, 2H), 4.84 (s, 1H), 4.51 (td, J=6.6, 13.2 Hz, 1H), 3.67 (s, 3H), 1.32 (d, J=6.6 Hz, 6H). m/z=265.1 (M+1)$^+$.

Example 3—Biological Assay

1321N1 human astrocytoma and HEK293 human embryonic kidney cells were stably transfected with human P2X2 and P2X3 receptor subunits to form heteromeric P2X2/3 channels and passaged in flasks. Additionally, HEK293 cells were stably transfected with human P2X3 receptor subunits to form homomeric P2X3 channels.

Approximately 24 hours before the FlexStation calcium fluorescence experiment, cells were released from their flasks, centrifuged and re-suspended in nutrient medium. The cells were aliquoted into black-wall, clear-bottom 96 well plates at a density of 25,000 cells per well and incubated overnight in a humidified, $CO_2$-enriched (5%) atmosphere at 37° C.

On the day of the experiment, cells were washed with assay buffer (calcium- and magnesium-free Hank's balanced salt solution, 20 mM HEPES, 2 mM $CaCl_2$); AB) and loaded with 4 M Fluo-4 (P2X2/3) or Calcium 6 (Molecular Devices, according to manufacturer's instructions; P2X3) calcium-sensitive fluorescent dye in 100 μL AB.

After 1 hour of dye loading at 37° C., 1321N1-hP2X2/3 cells were washed two times with AB and test compound or vehicle added to each well in a total volume of 150 μL AB. HEK-hP2X3 cells were not washed because the Calcium 6 dye kit includes an extracellular dye that quenches unabsorbed Calcium 6 dye; test compound or vehicle were added directly to the assay plates to achieve the appropriate concentration of test compound in a total volume of 150 μL AB.

After 20 minutes incubation at room temperature and protected from light, the assay plates were loaded into the FlexStation microplate reader and baseline fluorescence measured with an excitation wavelength of 485 nm and emission wavelength readings centered at 525 nm (515 nm cut off).

The agonist was dispensed by the FlexStation during fluorescence measurement to construct agonist activation and antagonist inhibition curves. The final agonist concentration for inhibition was 1 μM α,β-meATP for P2X3 and 3 M ATP for P2X2/3. Peak fluorescence was measured and curves generated using a four parameter nonlinear regression equation.

The data in the following Table were obtained using the assay referred to above.

| Compound # | Structure | Average pIC$_{50}$ P2X3 | Average pIC$_{50}$ P2X2/3 |
|---|---|---|---|
| 1 | 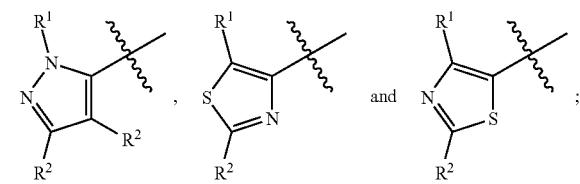 | 5.16 | <5 |
| 2 | 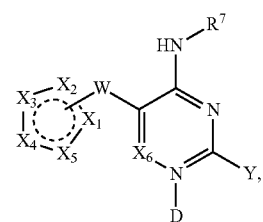 | 6.54 | 5.71 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:
1. A compound of Formula I:

I or a pharmaceutically acceptable salt thereof, wherein:
ring

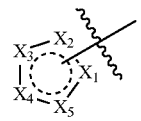

is selected from the group consisting of:

W is $CH_2$, NH, N—$C_{1-6}$alkylene, O or S;
$X_6$ is N;
Y is hydrogen or —NHR$^d$; wherein R$^d$ is selected from the group consisting of hydrogen, $C_{1-12}$alkyl, $C_{3-12}$cycloalkyl, aryl, and heteroaryl; wherein each of the $C_{1-12}$alkyl, $C_{3-12}$cycloalkyl, aryl, and heteroaryl is optionally substituted with one to three substituents independently selected from halogen, hydroxyl and $C_{1-6}$alkyl;
D is an optional oxygen;

each occurrence of $R^1$ is independently selected from the group consisting of hydrogen, hydroxyl, $C_{1-6}$alkyl, $C_{2-6}$alkenyl, and $C_{2-6}$alkynyl; wherein each of the $C_{1-6}$alkyl, $C_{2-6}$alkenyl, and $C_{2-6}$alkynyl is optionally substituted with one to three substituents independently selected from halogen and hydroxyl;

each occurrence of $R^2$ is independently selected from the group consisting of hydrogen, halogen, —NH—$R^f$, —C(O)—NHR$^f$, —C(O)—$C_{1-12}$alkyl, $C_{2-12}$alkenyl, $C_{2-12}$alkynyl, and —O—$C_{1-12}$alkyl;

each occurrence of $R^f$ is independently selected from the group consisting of hydrogen, $C_{1-12}$alkyl, hydroxyl, —SO$_2$—NH$_2$, and —SO$_2$—$C_{1-6}$alkyl; and $R^7$ is selected from the group consisting of hydrogen, $C_{1-12}$alkyl, and $C_{3-12}$cycloalkyl.

2. The compound of claim 1, or a pharmaceutically acceptable salt thereof, wherein:

W is CH$_2$ or O;

$X_6$ is N;

Y is hydrogen or —NHR$^d$; wherein $R^d$ is selected from the group consisting of hydrogen or $C_{1-6}$alkyl; wherein the $C_{1-6}$alkyl is optionally substituted with one to three substituents independently selected from halogen and hydroxyl;

D is absent;

each occurrence of $R^1$ is independently selected from the group consisting of hydrogen and $C_{1-6}$alkyl;

each occurrence of $R^2$ is independently selected from the group consisting of hydrogen, halogen, —NH—$R^f$, —C(O)—NHR$^f$, —C(O)—$C_{1-6}$alkyl, $C_{2-6}$alkenyl, and —O—$C_{1-6}$alkyl;

each occurrence of $R^f$ is independently selected from the group consisting of hydrogen, $C_{1-6}$alkyl, hydroxyl, —SO$_2$—NH$_2$, and —SO$_2$—$C_{1-6}$alkyl; and $R^7$ is selected from the group consisting of hydrogen and $C_{1-6}$alkyl.

3. The compound of claim 1, or a pharmaceutically acceptable salt thereof, having formulae Ia:

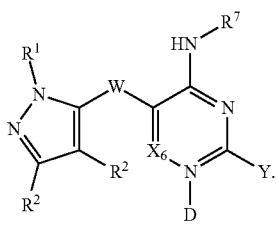

Ia

4. The compound of claim 1, or a pharmaceutically acceptable salt thereof, wherein:

W is CH$_2$ or O;

$R^1$ is selected from the group consisting of hydrogen and $C_{1-6}$alkyl;

$R^2$ is selected from the group consisting of hydrogen, halogen, —NH$_2$; —C(O)—NH$_2$, —C(O)—$C_{1-6}$alkyl, and —O—$C_{1-6}$alkyl; and $R^d$ is selected from the group consisting of hydrogen and $C_{1-6}$alkyl, or a pharmaceutically acceptable salt thereof.

5. The compound of claim 1, or a pharmaceutically acceptable salt thereof, having the following formula Ic or the following formula Id:

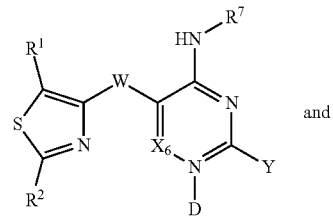

Ic and

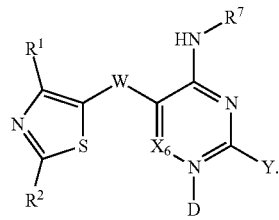

Id

6. The compound of claim 5 or a pharmaceutically acceptable salt thereof, wherein:

W is CH$_2$ or O;

$R^1$ is selected from the group consisting of hydrogen and $C_{1-6}$alkyl;

$R^2$ is selected from the group consisting of hydrogen, halogen, —NH$_2$, —C(O)—NH$_2$, —C(O)—$C_{1-6}$alkyl, and —O—$C_{1-6}$alkyl; and $R^d$ is selected from the group consisting of hydrogen and $C_{1-6}$alkyl, or a pharmaceutically acceptable salt thereof.

7. The compound of claim 1 or a pharmaceutically acceptable salt thereof, wherein W is O.

8. The compound of claim 1 or a pharmaceutically acceptable salt thereof, wherein W is CH$_2$.

9. A composition which comprises an inert carrier and a compound of claim 1 or a pharmaceutically acceptable salt thereof.

10. A compound of claim 1 or a pharmaceutically acceptable salt thereof for use in therapy.

11. The compound of claim 3 or a pharmaceutically acceptable salt thereof, wherin W is CH$_2$ or O;

$R^1$ is selected from the group consisting of hydrogen and $C_{1-6}$alkyl;

$R^2$ is selected from the group consisting of hydrogen, halogen, —NH$_2$; —C(O)—NH$_2$, —C(O)—$C_{1-6}$alkyl, and —O—$C_{1-6}$alkyl; and $R^d$ is selected from the group consisting of hydrogen and $C_{1-6}$alkyl.

12. The compound of claim 11 or a pharmaceutically acceptable salt thereof, wherein W is CH$_2$.

* * * * *

UNITED STATES PATENT AND TRADEMARK OFFICE
CERTIFICATE OF CORRECTION

| | | |
|---|---|---|
| PATENT NO. | : 11,591,315 B2 | Page 1 of 1 |
| APPLICATION NO. | : 17/179705 | |
| DATED | : February 28, 2023 | |
| INVENTOR(S) | : Ronald Charles Hawley et al. | |

It is certified that error appears in the above-identified patent and that said Letters Patent is hereby corrected as shown below:

On the Title Page

(73) Assignee:
Please delete "Merck Sharp & Dohme LLC"
And replace with:
"Afferent Pharmaceuticals, Inc."

Signed and Sealed this
Twenty-seventh Day of August, 2024

Katherine Kelly Vidal
*Director of the United States Patent and Trademark Office*